Figure 1:
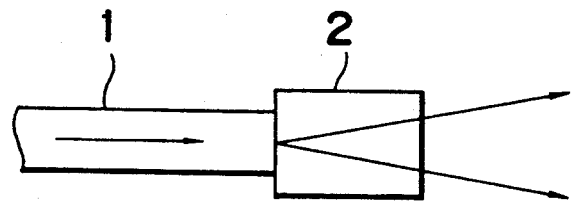

United States Patent [19]
Uemiya et al.

[11] Patent Number: 5,222,182
[45] Date of Patent: Jun. 22, 1993

[54] OPTICAL FIBER FOR LASER BEAM GUIDING FOR CURE

[75] Inventors: Takafumi Uemiya, Osaka; Shin-ichiro Niwa; Koro Yotsuya; Ichiro Sogawa; Shin-ichi Kanazawa, all of Osaka, Japan

[73] Assignee: Sumitomo Electric Industries, Ltd., Osaka, Japan

[21] Appl. No.: 465,161

[22] PCT Filed: Jun. 6, 1989

[86] PCT No.: PCT/JP89/00573
§ 371 Date: Feb. 6, 1990
§ 102(e) Date: Feb. 6, 1990

[87] PCT Pub. No.: WO89/12239
PCT Pub. Date: Dec. 14, 1989

[30] Foreign Application Priority Data
Jun. 6, 1988 [JP] Japan .............................. 63-74908[U]

[51] Int. Cl.⁵ ............................. G02B 6/00; G02B 6/36
[52] U.S. Cl. .................................... 385/122; 359/326; 385/31; 385/123
[58] Field of Search ............................ 307/425-430; 350/96.12, 96.15, 96.29, 96.3, 96.31, 96.32, 96.33, 96.34; 359/326-332; 385/31, 38, 50, 122, 123

[56] References Cited

U.S. PATENT DOCUMENTS

| | | |
|---|---|---|
| 4,538,278 | 8/1985 | Gergely ......................... 307/427 X |
| 4,612,456 | 9/1986 | Gergely ............................ 307/425 |
| 4,867,510 | 9/1989 | Dobson ............................ 307/427 |
| 4,909,595 | 3/1990 | Okazaki et al. .................. 350/96.29 |
| 4,909,609 | 3/1990 | McDowell .................. 350/96.32 X |
| 4,923,277 | 5/1990 | Okazaki et al. ................. 350/96.29 |
| 4,973,125 | 11/1990 | Normandin ................. 350/96.12 X |

FOREIGN PATENT DOCUMENTS

| | | |
|---|---|---|
| 0254921 | 2/1988 | European Pat. Off. . |
| 51-21838 | 2/1976 | Japan . |
| 63-78106 | 4/1988 | Japan . |
| 63-163436 | 7/1988 | Japan . |
| 2154364 | 9/1985 | United Kingdom . |

OTHER PUBLICATIONS

N. Uesugi et al, "Efficient second-harmonic generation in three-dimensional LiNbO3 optical waveguide", APPLIED PHYSICS LETTERS, vol. 29, No. 9, Nov. 1, 1976, New York US, pp. 572-574.

*Primary Examiner*—Akm E. Ullah
*Attorney, Agent, or Firm*—Cushman, Darby & Cushman

[57] ABSTRACT

An optical fiber for laser beam guiding comprising a secondary non-linear optical element at one tip thereof can irradiate a lesion portion with a short wavelength beam useful for cure, since the non-linear optical element converts a long wavelength beam transmitted through the optical fiber to the short wavelength laser beam.

1 Claim, 1 Drawing Sheet

OPTICAL FIBER FOR LASER BEAM GUIDING FOR CURE

FIELD OF THE INVENTION

The present invention relates to an optical fiber for laser beam guiding. In particular, the present invention relates to an optical fiber for laser beam guiding comprising a secondary non-linear optical element, which fiber can be used in, for example, a catheter for lasing in which laser beam irradiation cures a lesion portion.

BACKGROUND OF THE INVENTION

An optical fiber for laser beam guiding is used in a catheter for the use of lasing which removes a lesion portion such as a thrombus in a blood vessel, which a practitioner cannot directly approach, by means of irradiating with a laser beam and vaporizing the portion. In such the lasing catheter, the optical fiber is used to transmit the laser beam to a tip of the catheter with a low beam loss.

In the meantime, in the lasing, it is required for the cure to use a beam having a short wavelength which has a large amount of energy and is sufficiently absorbed in a tissue in vivo.

However, a threshold value of destruction of the optical fiber for laser beam guiding is sharply reduced as the wavelength of the laser beam injected therein becomes short. For example, in the case of quartz, it is said that while the threshold value of destruction for the fundamental wave (1.064 $\mu$m) of YAG laser beam is 130 GW/cm$^2$, the triple-frequency wave (0.355 $\mu$m) is reduced to one fifth of that for the fundamental wave.

Thus, even though lasing with a beam having the short wavelength such as an ultraviolet light (UV light) is effective for the cure, it has not been sufficiently utilized since the threshold value of destruction for the laser beam having the short wavelength is low.

OBJECT OF THE INVENTION

It is an object of the present invention to provide an optical fiber for laser beam guiding which makes it possible to irradiate with a beam having a short wavelength which has not been conventionally used due to a low threshold value of destruction for the short wavelength laser beam.

DISCLOSURE OF THE INVENTION

An optical fiber for laser beam guiding according to the present invention is characterized in that it comprises a secondary non-linear optical element at its one tip.

Any known secondary non-linear optical material can be used to form said secondary non-linear optical element. For example, an inorganic material such as LiNbO$_3$, LiIO$_3$, KH$_2$PO$_4$ (KDP), KTiOPO$_4$ (KTP), Ba$_2$NaNb$_5$O$_{15}$ or an organic material such as 2-methyl-4-nitroaniline (MNA), urea, m-nitroaniline can be used. When an ultraviolet light is generated with wavelength conversion, desired is the material such as KDP which shows an absorption on the shorter wavelength side.

The non-linear optical material is not limited to one of a crystal form but a polymer material in which the non-linear optical material is dispersed may be used. In addition, the non-linear optical element may be in the form of a bulk crystal which automatically phase-matches or in the form which phase-matches by means of a waveguide configuration.

The optical fiber may be a multi-mode fiber or a single-mode fiber. In order to transmit a wavelength converted beam with a high efficiency, the single-mode fiber is preferred. The wavelength resulted from the wavelength conversion may be one of any wave such as a double-frequency wave, a triple-frequency wave and a quadruple-frequency wave. For example, when YAG laser is used, the combinations shown in the below table are possible, and any suitable combination can be optionally selected depending on curing effects. In particular, the fiber has not been known which can transmit an ultraviolet light such as the quadruple-frequency wave.

TABLE

| Injected laser beam | Converted beam |
| --- | --- |
| Fundamental wave (1.06 $\mu$m) | Double-frequency wave (0.53 $\mu$m) |
| Fundamental wave + double-frequency wave | Triple-frequency wave (0.355 $\mu$m) |
| Double-frequency wave | Quadruple-frequency wave (0.266 $\mu$m) |

When the laser beam having a long wavelength for which has the high threshold value of destruction is high is injected into the optical fiber for laser beam guiding, the laser beam is radiated as a beam having a short wavelength by means of the wavelength conversion of the secondary non-linear optical element disposed at the tip of the fiber after transmitted without destruction of the fiber.

EMBODIMENTS

The embodiments of the optical fiber according to the present invention will be hereinafter described with reference to the accompanying drawings. Referring to the drawings, FIGS. 1–4 show preferable embodiments of the optical fiber for laser beam guiding according to the present invention.

FIG. 1 schematically shows the fiber tip portion and the non-linear optical element of the first embodiment of the optical fiber for laser beam guiding according to the present invention. In the embodiment shown in FIG. 1, at the tip of the optical fiber 1 which transmits a beam having a long wavelength (wavelength: $\lambda_1$), the non-linear optical element 2 comprising the material which shows the secondary non-linear optical effect is disposed such that the injected surface of the element faces to the end surface of the optical fiber 1.

With such the optical fiber for laser beam guiding, when the laser beam having the long wavelength $\lambda_1$ is injected from a laser beam source (not shown), the injected beam enters the non-linear optical element 2 after it is transmitted through the optical fiber 1 to the tip thereof and radiated from the end surface of the tip.

The laser beam which enters the non-linear optical element 2 is freely transmitted therethrough and then radiated therefrom after wavelength-conversion to a beam having a short wavelength of $\frac{1}{2}\lambda_1$. In such the case, usually the long wavelength beam having a wavelength of $\lambda_1$ and the short wavelength beam having a wavelength of $\frac{1}{2}\lambda_1$ are present together since there remains a beam which is radiated without suffering from wavelength-conversion.

In the drawings, a solid line with an arrow shows a light path.

Figure 2:
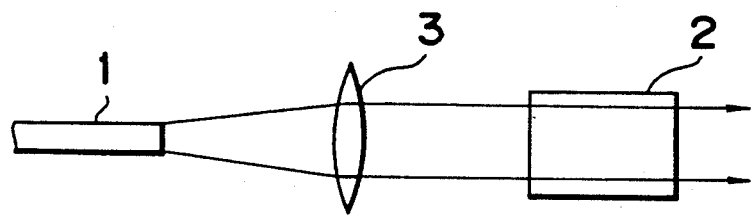

In the second embodiment shown in FIG. 2, a convex lens 3 is disposed on the light path between the end surface at the tip of the optical fiber 1 and the non-linear optical element 2. The laser beams radiated from the fiber 1 are focused by the convex lens 3 to prevent decrease of the illuminance.

This embodiment is suitable in the field of, for example, the catheter for the lasing since the illuminance of the beam is not reduced.

Figure 3:
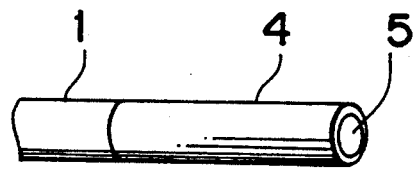

In the optical fiber for laser beam guiding shown in FIG. 3, the non-linear optical element in the form of a light waveguide having substantially the same outer diameter as that of the optical fiber 1 is disposed on the end surface of the tip portion of the optical fiber 1.

This non-linear optical element comprises a cylindrical cladding 4 and a core 5 comprising the non-linear optical material. Since the non-linear optical element is in the form of the light waveguide, non-linear optical conversion is possible over a considerable long distance if the converted short wavelength beam can be phase-matched, whereby an efficiency of the conversion can be increased.

Figure 4:
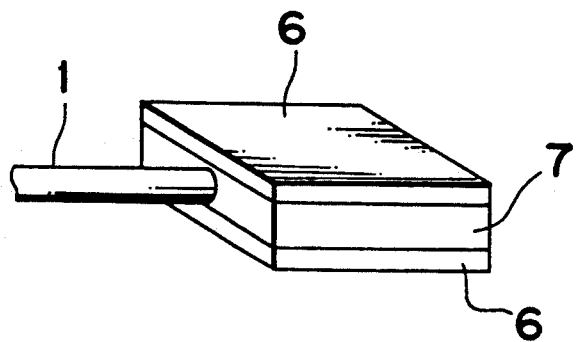

In the optical fiber for laser beam guiding shown in FIG. 4, the sandwich-type non-linear optical element is attached to the radiating end surface of the optical fiber 1, in which element the waveguiding portion 7 comprising the non-linear optical material is sandwiched with a pair of claddings 6 and 6 in the form of a plate.

The optical fiber for laser beam guiding according to the present invention comprises the secondary non-linear optical element at the tip of the optical fiber. Therefore, the long wavelength laser beam can be converted to the short wavelength laser beam by the secondary non-linear optical element disposed at the tip of the optical fiber, whereby a lesion portion can be irradiated with such the short wavelength laser beam useful for the cure as the radiated beam.

What is claimed is:

1. An optical fiber for laser beam guiding during a medical procedure comprising;
   an optical fiber; and
   a secondary non-linear optical element disposed at one tip of the optical fiber, wherein the non-linear optical element is in the form of a light waveguide which comprises a cylindrical cladding having an outer diameter substantially the same as that of the optical fiber and a core comprising a secondary non-linear optical material.

* * * * *